(12) United States Patent
Hwang et al.

(10) Patent No.: US 12,134,755 B2
(45) Date of Patent: Nov. 5, 2024

(54) CELL STIMULATION AND CULTURE PLATFORM USING ULTRASONIC HOLOGRAM

(71) Applicant: DAEGU GYEONGBUK INSTITUTE OF SCIENCE AND TECHNOLOGY, Daegu (KR)

(72) Inventors: Jae Youn Hwang, Daegu (KR); Moon Hwan Lee, Gyeongsan-si (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 294 days.

(21) Appl. No.: 17/960,999

(22) Filed: Oct. 6, 2022

(65) Prior Publication Data

US 2023/0108076 A1    Apr. 6, 2023

(30) Foreign Application Priority Data

Oct. 6, 2021  (KR) .......................... 10-2021-0132152

(51) Int. Cl.
| | |
|---|---|
| *C12M 1/42* | (2006.01) |
| *C12M 1/00* | (2006.01) |
| *C12M 3/00* | (2006.01) |
| *C12N 13/00* | (2006.01) |
| *G01N 29/06* | (2006.01) |
| *G03H 3/00* | (2006.01) |

(52) U.S. Cl.
CPC .............. *C12M 1/42* (2013.01); *C12M 23/58* (2013.01); *C12M 35/04* (2013.01); *C12N 13/00* (2013.01); *G01N 29/0663* (2013.01); *G03H 3/00* (2013.01)

(58) Field of Classification Search
CPC .......... C12M 1/42; C12M 3/00; C12M 23/58; C12M 35/04; C12N 13/00; G01N 29/0663; G03H 3/00
See application file for complete search history.

(56) References Cited

U.S. PATENT DOCUMENTS

2021/0054330 A1*  2/2021  Takahara ................. C12Q 3/00

FOREIGN PATENT DOCUMENTS

| JP | 2005160340 A | * | 6/2005 | .............. C12M 3/00 |
|---|---|---|---|---|
| KR | 20130101340 A | * | 9/2013 | .............. C12M 1/42 |
| KR | 10-2015-0125350 | | 11/2015 | |
| KR | 10-2020-0098999 | | 8/2020 | |
| KR | 10-2283276 | | 7/2021 | |

* cited by examiner

*Primary Examiner* — Nguyen Q. Ha
(74) *Attorney, Agent, or Firm* — LEX IP MEISTER, PLLC

(57) ABSTRACT

According to the present disclosure, there is provided a cell stimulation and culture platform using a ultrasonic hologram, including a culture vessel in which a culture well with an open lower portion is formed; a transmission sheet which is installed to cover a lower surface of the culture vessel and where a biological sample is seated; a platform body that is filled with a liquid medium and an open upper end is covered by the transmission sheet; an ultrasonic transducer that is installed inside the platform body in a state of being spaced apart from the biological sample; and an ultrasonic hologram lens that is installed on the ultrasonic transducer, and spatially modulates the phase of the ultrasonic waves using a surface structure designed to have different height distributions to focus the ultrasonic waves in a set pattern shape on a target surface on which the biological sample is located.

11 Claims, 9 Drawing Sheets

Result of Deep learning-based algorithm

CELL STIMULATION AND CULTURE PLATFORM USING ULTRASONIC HOLOGRAM

CROSS-REFERENCE TO RELATED APPLICATION

This application is based on and claims priority under 35 U.S.C. § 119 to Korean Patent Application No. 10-2021-0132152, filed on Oct. 6, 2022, in the Korean Intellectual Property Office, the disclosure of which is incorporated by reference herein in its entirety.

BACKGROUND

1. Field

One or more embodiments relate to a cell stimulation and culture platform using an ultrasonic hologram, and more particularly, to a cell stimulation and culture platform using an ultrasonic hologram that may be stimulated and cultured by irradiating cells with ultrasonic waves in a desired shape using the ultrasonic hologram.

2. Description of the Related Art

Recently, research on a cell culture system including an ultrasonic transducer that may simultaneously perform ultrasonic stimulation providing and culturing of cells has been actively conducted.

In general, a cell stimulation system using ultrasonic waves includes a plurality of ultrasonic transducers and a plurality of cell accommodating tubes disposed above each of the ultrasonic transducers. At this time, each ultrasonic transducer operates to stimulate the cells accommodated in each accommodating tube by using ultrasonic waves.

Conventionally, a cell stimulation system using an ultrasonic transducer including a plurality of array-type ultrasonic elements has been disclosed. The system has a plurality of cell accommodating units corresponding to the plurality of ultrasonic elements, respectively, and has a structure capable of selectively stimulating cells disposed corresponding to the ultrasonic elements by operating a selected ultrasonic element among the plurality of ultrasonic elements.

However, in the case of the above-described structure, all wavelengths from each ultrasonic element are propagated with the same phase and the cell is irradiated therewith. In addition, selective stimulation is possible for each well of a cell culture dish, but it is impossible to control a stimulation range.

In addition, since the ultrasonic transducer is located just below the cell, when ultrasonic waves are generated from the ultrasonic transducer, the mechanical vibration of the transducer may affect the cell, which may cause an unintended effect during cell culture.

The technology that is the background of the present disclosure is disclosed in Korean Patent Application Laid-Open No. 10-2015-0125350 (published on Nov. 9, 2015).

SUMMARY

An object of the present disclosure is to provide a cell stimulation and culture platform using an ultrasonic hologram that may selectively stimulate and culture a biological sample according to a corresponding shape by irradiating the biological sample with ultrasonic waves of a desired shape by using the ultrasonic hologram.

The present disclosure provides a cell stimulation and culture platform using a ultrasonic hologram, including a culture vessel in which a culture well with an open lower portion is formed; a transmission sheet which is installed to cover a lower surface of the culture vessel and where a biological sample is seated on a surface portion corresponding to the culture well; a platform body of which an inner space is filled with a liquid ultrasonic medium and an open upper end is covered by the transmission sheet; an ultrasonic transducer that is installed at an inner lower end portion of the platform body in a state of being spaced apart from the biological sample by a set distance to generate ultrasonic waves upward; and an ultrasonic hologram lens that is installed on the ultrasonic transducer, transmits the incident ultrasonic waves to a target surface on which the biological sample is located through the ultrasonic medium, and spatially modulates the phase of the ultrasonic waves using a surface structure designed to have different height distributions to focus the ultrasonic waves in a set pattern shape on the target surface.

In addition, the biological sample may be located on the target surface and cultured in the set pattern shape.

In addition, the transmission sheet may be formed of a Mylar sheet or a PDMS sheet.

In addition, the ultrasonic medium may be water or a material of which ultrasonic transmittance is greater than or equal to a threshold.

In addition, the ultrasonic hologram lens may be designed based on a deep learning model that derives a phase distribution image to which a phase value for each pixel is assigned corresponding to an input of a target image in a form of the set pattern shape drawn, and a design thickness for each unit area of the lens surface may vary according to a phase value for each pixel and a lens material.

In addition, the ultrasonic hologram lens may be manufactured by a 3D printing method through a three-dimensional mesh model generated according to the thickness of each unit area of the lens surface.

In addition, the deep learning model may perform deep learning of a target image where an amplitude value of a target acoustic field is individually assigned to each pixel corresponding to the set pattern shape, and may output a phase value for each pixel as a two-dimensional phase distribution image.

In addition, the phase value for each pixel is determined in the $-\pi$ to $\pi$ ranges.

In addition, the deep learning model may be learned by using a loss between an amplitude value $A_{ASM}(x,y)$ of the acoustic field for each pixel derived on the target surface through an Angular Spectrum Method (ASM) or an arbitrary ultrasonic waves simulation based on the phase value for each pixel, and an amplitude value $A_{goal}(x,y)$ of the acoustic field for each pixel of the target image.

In addition, a loss function corresponding to an error between the $A_{goal}(x,y)$ and the $A_{ASM}(x,y)$ may be defined by the following equation.

$$L(A_{goal}, A_{ASM}) = 1 - \left( \frac{\sum_{x,y} A_{goal} \circ A_{ASM}}{\sqrt{\left[\sum_{x,y} A_{goal}^2\right]\left[\sum_{x,y} A_{ASM}^2\right]}} \right)$$

Here, L is the loss function, is a product between matrix elements, and $\Sigma_{x,y}(\cdot)$ is a sum of values $(\cdot)$ obtained for each pixel.

In addition, the phase value of each pixel in the phase distribution image may be smoothed for each sector in accordance with a processing resolution of the 3D printer, and the phase value distribution for each pixel in the smoothed state may be utilized for deep learning.

According to the present disclosure, by irradiating an ultrasonic hologram of a specific shape with respect to a biological sample such as cells in a culture well by using an ultrasonic hologram, the cells may be selectively stimulated and cultured according to the shape, and may be induced to gather and grow in a specific shape in the culture well.

The present disclosure uses the ultrasonic hologram lens designed to have the surface structure with different height distributions based on deep learning to spatially modulate the phase of the ultrasonic signal to irradiate the target surface where the cells are located with the specific pattern-shaped ultrasonic waves. Therefore, it has an advantage of being able to selectively stimulate cells and adjust the stimulation range, even within the same culture well.

In addition, in the case of the present disclosure, the ultrasonic transducer is installed to be spaced apart from the biological sample, and the separated space is filled with a liquid medium such as water so that only the ultrasonic signal may affect the cells. Therefore, it is possible to minimize affecting due to the mechanical vibration of the ultrasonic waves during cell culture.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1A:
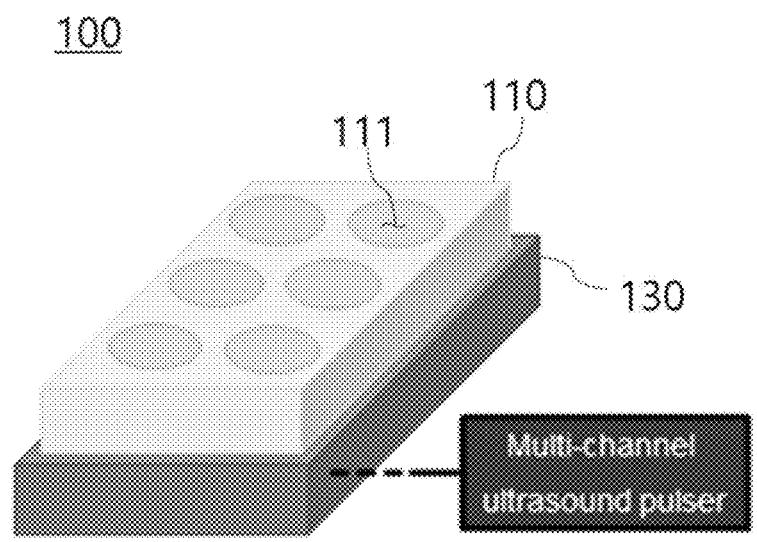
FIG. 1(a) and FIG. 1(b) are views illustrating a configuration of a cell stimulation and culture platform using an ultrasonic hologram according to an embodiment of the present disclosure.

Then, with reference to the accompanying drawings, embodiments of the present disclosure will be described in detail so that those of ordinary skill in the art to which the present disclosure pertains may easily implement them. However, the present disclosure may be implemented in several different forms and is not limited to the embodiments described herein. In addition, in order to clearly explain the present disclosure in the drawings, parts irrelevant to the description are omitted, and similar reference numerals are attached to similar parts throughout the specification.

Throughout the specification, when a part is "connected" to another part, this includes not only a case of being "directly connected" but also a case of being "electrically connected" with another element interposed therebetween. Also, when a part "includes" a certain component, it means that other components may be further included, rather than excluding other components, unless otherwise stated.

FIG. 1 is a view illustrating a configuration of a cell stimulation and culture platform using an ultrasonic hologram according to an embodiment of the present disclosure.

Figure 1B:
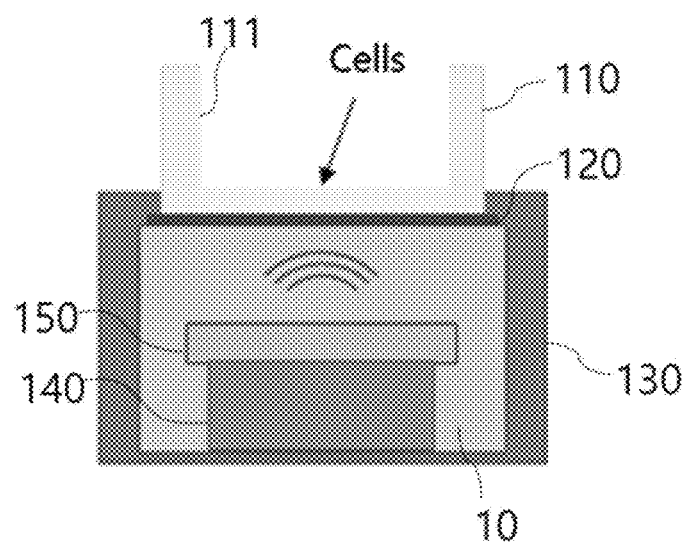

FIG. 1(a) schematically illustrates an appearance of the entire platform, and illustrates a state in which six culture wells are formed in a culture vessel 110. Here, FIG. 1(b) illustrates a cross-section of a platform body based on a single culture well for convenience of description.

As illustrated in FIG. 1, a cell stimulation and culture platform 100 using an ultrasonic hologram according to an embodiment of the present disclosure includes the culture vessel 110, a transmission sheet 120, a platform body 130, an ultrasonic transducer 140, and an ultrasonic hologram lens 150.

The culture vessel 110 is formed with at least one culture well 111. In the embodiment of the present disclosure, the culture well 111 has a structure in which a lower portion is open unlike a general culture vessel. In the case of the embodiment of the present disclosure, instead of using a structure in which the lower portion of the culture well 111 is perforated, the lower portion is covered with the transmission sheet 120 capable of ultrasonic transmission.

The transmission sheet 120 is installed to cover a lower surface of the culture vessel 110, and biological samples (for example: cell samples (Cells)) are seated on a surface portion corresponding to the culture well 111. That is, when the transmission sheet 120 is laminated on a lower side of the culture vessel 110, the cells are placed on the surface portion exposed by the culture well 111.

The transmission sheet 120 is formed to cover the entire lower surface of the culture vessel 110, and may be formed of an ultrasonic transmission sheet including a Mylar sheet or a polydimethylsiloxane (PDMS) sheet.

Conventional cell culture dish materials such as plastic and glass have ultrasonic attenuation and reflection effects, but in the case of the embodiment of the present disclosure, the lower portion of the culture well 111 is implemented as a perforated structure, and at the same time, the lower portion is covered by the Mylar sheet or the PDMS sheet to eliminate concerns about related effects.

The culture vessel 110 is installed above the platform body 130 in a state in which the lower end is blocked with the transmission sheet 120.

An upper end portion of the platform body 130 is covered by the transmission sheet 120. The upper end portion of the platform body 130 is open, and the transmission sheet 120 and the culture vessel 110 are sequentially placed on the open upper end portion.

An inner space of the platform body 130 is filled with a liquid ultrasonic transmission medium 10 (hereinafter, referred to as an ultrasonic medium) such as water. Although the embodiment of the present disclosure uses water as a sound transmitting material, the present disclosure is not necessarily limited thereto, and various materials capable of transmitting an ultrasonic signal without loss (for example: a material having an ultrasonic transmittance greater than or equal to a threshold value) may be used.

The ultrasonic transducer 140 and the ultrasonic hologram lens 150 are installed in the inner space of the platform body 130.

The ultrasonic transducer 140 is installed in the lower inner portion of the platform body 130 in a state of being spaced apart from the biological samples (Cells) by a set distance, and generates ultrasonic waves upward. The ultrasonic transducer 140 may be implemented as a single element ultrasonic transducer, and may be manufactured as a piezoelectric transducer (PZT), a piezoelectric micromachined ultrasonic transducer (pMUT), a capacitive micromachined ultrasonic transducer (cMUT), or the like. The frequency may be changed according to the stimulus resolution, the height of the stimulus, and the like.

The ultrasonic transducer 140 is spaced apart from the biological samples (Cells) by a set distance (for example: 5 mm) as illustrated in FIG. 1(b). The ultrasonic medium 10 (water) exists in the spaced apart space. According to this, only the ultrasonic signal may affect the cells without the mechanical vibration effect of the transducer, and the space created by the set distance is filled with a sound-transmitting material such as water so that the ultrasonic wave may be transmitted without loss.

That is, the mechanical vibration caused by the ultrasonic generation of the ultrasonic transducer 140 is canceled by the ultrasonic medium 10 such as water, so that the vibration is not transmitted to the cells and only the effect of the ultrasonic signal is transmitted, so that the effect by the mechanical vibration rather than the ultrasonic waves is eliminated, and a possibility of unintended consequences may be excluded.

The ultrasonic signal generated by the ultrasonic transducer 140 is transmitted through the ultrasonic hologram lens 150 located immediately above.

The ultrasonic hologram lens 150 is installed on the ultrasonic transducer 140 and transmits the ultrasonic waves incident from the ultrasonic transducer 140 to the target surface on which the biological samples (Cells) are located through the ultrasonic medium 10.

At this time, the ultrasonic hologram lens 150 has a surface structure designed to have a different height distribution for each unit area, and spatially modulates the ultrasonic waves through this surface structure to focus the ultrasonic waves in a set pattern shape on the target surface.

Accordingly, the biological samples (Cells) located on the target surface are cultured in the set pattern shape. Here, the set pattern shape may have various forms, and may be remarkably diverse, such as a desired specific pattern (design), character (letter) shape, polygon, circle, and geometric pattern.

Therefore, the embodiment of the present disclosure enables selective stimulation of cells in the same well through ultrasonic hologram irradiation. When the ultrasonic waves are collected, a difference in energy is generated to generate a force. In the present disclosure, by using this force as a non-contact forceps, an energy difference is induced through the ultrasonic hologram, and the force is applied to the cells to induce the cells to gather and grow in a desired shape.

The ultrasonic transducer 140 and the ultrasonic hologram lens 150 may be configured as a plurality of channels for each culture well in the platform body 130. In addition, a signal applying unit for applying an ultrasonic waves signal of a set frequency and size may be installed outside or inside the platform and connected to each ultrasonic transducer. In addition, by designing the ultrasonic hologram lens 150 differently for each culture well, the cells may be stimulated and cultured in different pattern shapes in each culture well 111.

As described above, in the present embodiment, the platform capable of culturing or stimulating the cells by selectively irradiating a desired portion with the ultrasonic waves using the ultrasonic hologram is provided. The ultrasonic hologram refers to a technology that three-dimensionally handles ultrasonic energy by using the offset between several ultrasonic waves.

The ultrasonic waves are propagated in the form of a plane wave or a spherical wave, and if the difference in the transmission start time, that is, the phase of the transmission signal, is changed intentionally at various locations, it may be collected or moved to a desired point. By using this principle, if a lens with a different height distribution is intentionally placed in front of a single element ultrasonic transducer, the ultrasonic waves may be collected at a desired point and may be made into a certain shape.

The ultrasonic hologram lens 150 may be formed of a general lens material, and may be conveniently manufactured by a 3D printing method. By using the 3D printing method, a lens surface structure designed with different height distributions may be quickly and easily implemented, and a desired surface structure may be implemented with high resolution.

In the embodiment of the present disclosure, the ultrasonic hologram lens 150 may be designed to have a surface structure with different height distributions based on the phase determined by the deep learning algorithm, and may be easily manufactured through a 3D printer.

A representative algorithm for determining the phase for transmitting the ultrasonic waves to form a desired shape is a Gerchberg-Saxton (GS) algorithm, but the GS algorithm is time-consuming because it repeatedly propagates and back-propagates and optimizes the phase distribution, and the time may be further increased depending on the simulation method.

In the present disclosure, an algorithm for deriving the phase distribution at once based on deep learning is used, and the structure of the ultrasonic hologram lens 150 is designed based on the phase distribution derived by the deep learning algorithm.

The deep learning-based phase determination algorithm is based on a U-Net, extracts spatial features of the desired shape to be formed, and informs the phase distribution to be transmitted.

The learning method is such that when a picture of a desired shape is given to the U-Net and the phase distribution is output accordingly from the U-Net, the result thereof is propagated to the target plane through simulation, the propagation result is compared with the input picture, and learning proceeds to form a similar shape. Therefore, learning proceeds so that an error between the propagation result and the input picture is equal to or less than a threshold. After learning proceeds, since the actual phase prediction is not an iterative optimization method, the speed thereof is very fast, and it is possible to optimize not only the shape formation but also uniformity, energy intensity, and the like by changing the learning data and loss function. The phase distribution determined through the algorithms described above is a phase of a two-dimensional ultrasonic signal, and a range of values is (−π,π). Hereinafter, a deep learning-based phasing algorithm will be described in more detail.

Figure 2:
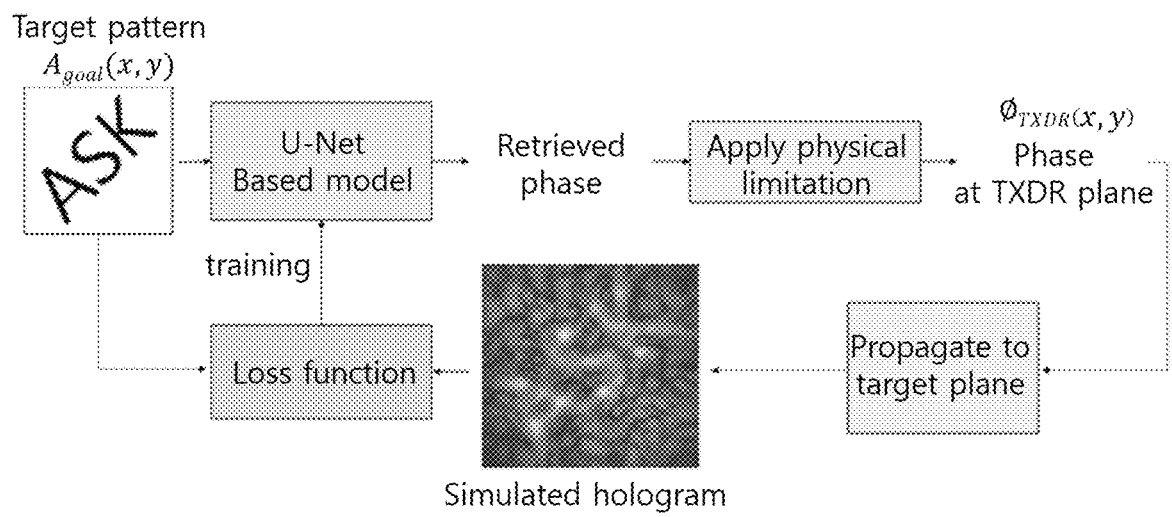
FIG. 2 is a diagram illustrating a learning principle of a deep learning algorithm used for lens design in an embodiment of the present disclosure.
Figure 3:
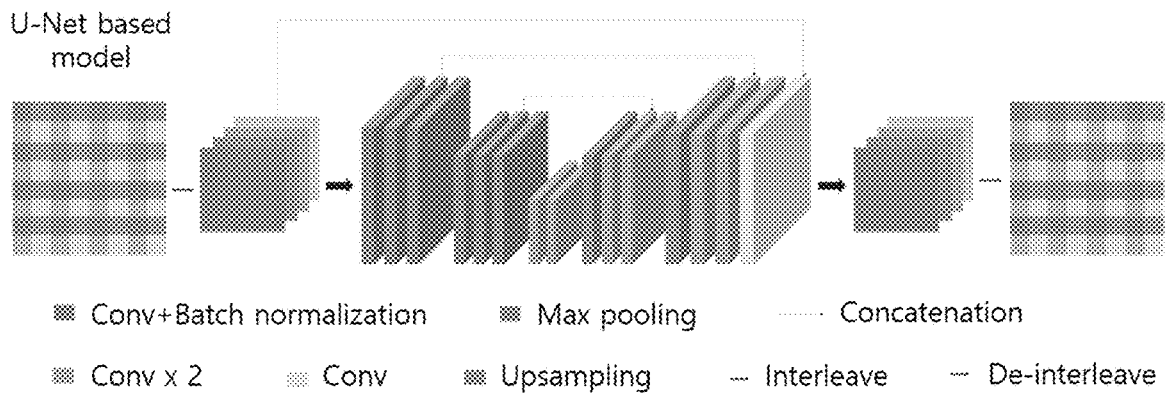
FIG. 3 is a diagram illustrating in detail a structure of a U-Net illustrated in FIG. 2.

FIG. 2 is a diagram for explaining the learning principle of the deep learning algorithm used for lens design in the embodiment of the present disclosure, and FIG. 3 is a diagram illustrating the structure of the U-Net illustrated in FIG. 2 in detail.

In the embodiment of the present disclosure, the ultrasonic hologram lens 150 is designed based on the deep learning algorithm. Here, in order to consider the correlation between spatial information between an input and an output, the deep learning algorithm is implemented including a widely used U-Net-based model developed for semantic image segmentation as illustrated in FIG. 2.

A detailed structure of the U-Net model refers to FIG. 3. The U-Net learns the spatial context of the input image based on a convolution layer and may give the related output in units of pixels. Therefore, it was used in the development of this algorithm to determine the phase of the transmission signal forming the desired pattern as the input.

As illustrated in FIG. 2, the deep learning model used in the embodiment of the present disclosure derives the phase distribution image in a form in which a phase value for each pixel is assigned as an output value when a target image in a form in which a set pattern shape is drawn is received. In this case, the target image represents an image in which a pattern to be formed at a desired distance point (target surface) is drawn.

In the case of FIG. 2, an example of the deep learning by inputting the target image on which a character 'ASK' is drawn into the U-Net is illustrated. The output of the U-Net model is also in the form of an image. In this case, the output of the model is a phase distribution image, and has a form in which a phase value for each pixel is assigned in color as illustrated in FIG. 4(b) which is described later.

The ultrasonic hologram lens 150 is designed based on the deep learning model that derives the phase distribution image corresponding to the input of the target image in the form of which the set pattern shape is drawn as described above. The phase value for each pixel in the phase distribution image is determined within the range of −π and π. Here, each pixel in the phase distribution image may correspond to each unit area constituting the lens surface of the ultrasonic hologram lens 150. The lens surface may be divided into a plurality of unit areas having the same rectangular shape as the pixel.

In addition, the ultrasonic hologram lens 150 according to the embodiment of the present disclosure has a surface structure designed to have a different height distribution, and this surface structure is implemented by varying the height of each unit area constituting the lens surface.

In this case, the design height (thickness) of the unit area may be determined according to the phase value of the pixel. Of course, for this, an information table, in which the height (thickness) value of the lens matched thereto for each of a plurality of phase values between −π and π is previously stored, may be utilized. Here, in consideration of a sound wave speed of a material to be used as the lens, an information table may be individually constructed and utilized for various materials of the lens.

As described above, in the case of the embodiment of the present disclosure, the design thickness for each unit area of the lens surface may be determined based on the phase value for each pixel in the phase distribution image determined in the U-Net corresponding to the input image and the constituting material of the lens, and based on this, the ultrasonic hologram lens 150 may be manufactured.

Here, the horizontal×vertical resolution of the pixel in the actual image and the horizontal×vertical processing resolution of the 3D printer for lens production may be different. In general, the processing resolution of the 3D printer is lower than the resolution of the pixel. Accordingly, the embodiment of the present disclosure may include a process of lowering the resolution of the phase distribution image by averaging the phase values of each pixel in the phase distribution image for each sector of a predetermined size and performing a smoothing process.

In this case, the size of the area of the sector may be determined according to a resolution difference between the image resolution and the processing resolution. For example, if both the horizontal and vertical resolutions of the image are three times higher than the processing resolution of the 3D printer, the sector size is set to a size of 3×3 pixels, and all the phase values of 9 pixels within the same sector may be replaced the average phase value thereof. This will be described in detail later with reference to FIG. 5(a) and FIG. 5(b).

FIGS. 4(a) to 4(d) are diagrams illustrating a process of designing and manufacturing the ultrasonic hologram lens according to the embodiment of the present disclosure.

Figure 4A:
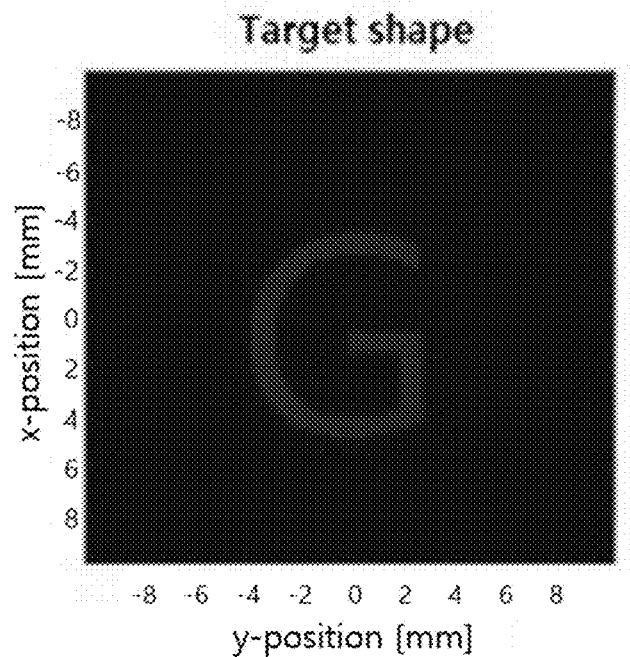
FIGS. 4(a) to 4(d) are diagrams illustrating a process of designing and manufacturing an ultrasonic hologram lens according to an embodiment of the present disclosure.
Figure 4B:
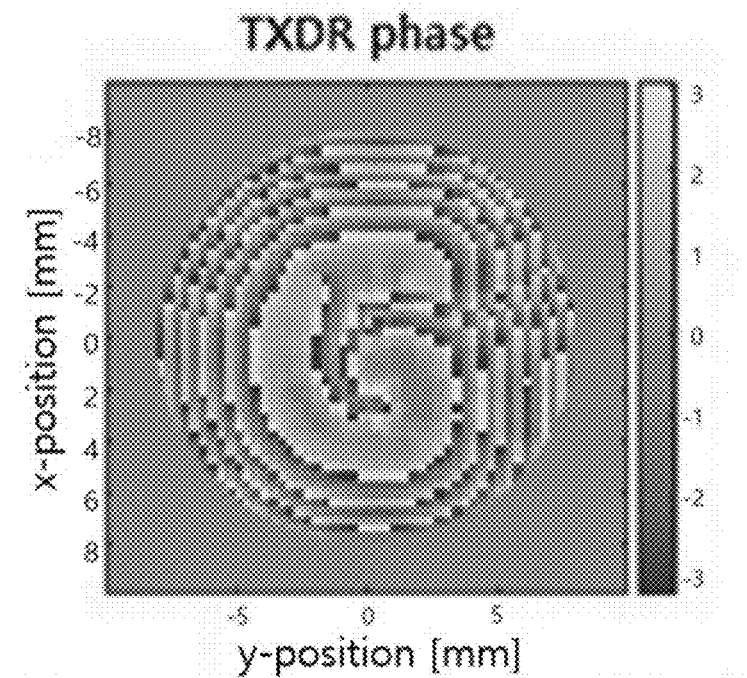

FIG. 4(a) illustrates an example of the target image input to the U-Net. The target image is drawn with the letter G. FIG. 4(b) illustrates the phase distribution image output from the U-Net when the target image is input. Here, it is assumed that the U-Net has been learned in advance. The phase value of each pixel in the phase distribution image is expressed in a color form, and a different color is assigned to each phase value. In this case, the closer the phase value is to −π (−180°), the more blue it is, and the closer to +π (+180°), the more yellow it is.

Figure 4C:
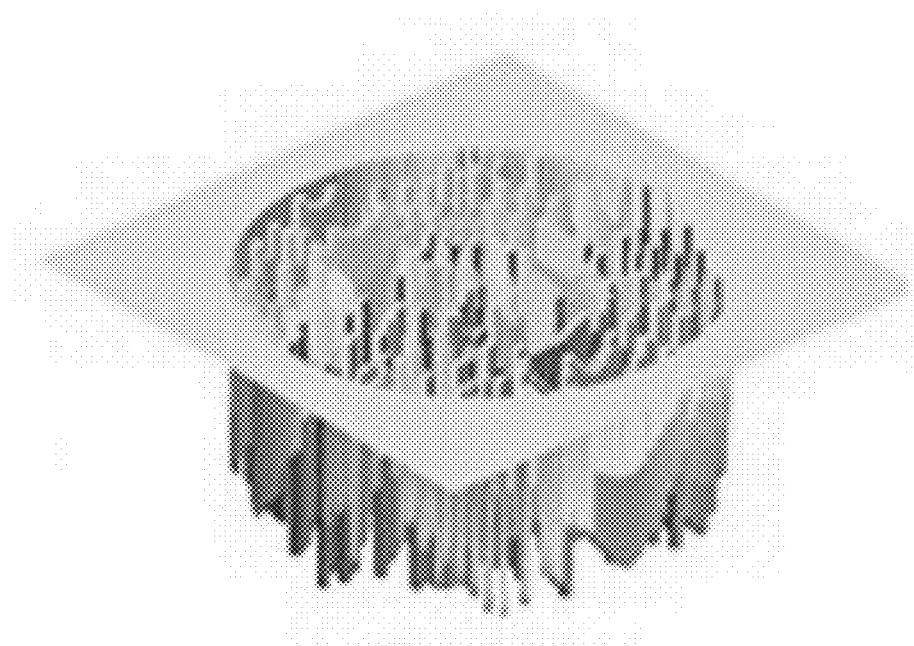
Figure 4D:
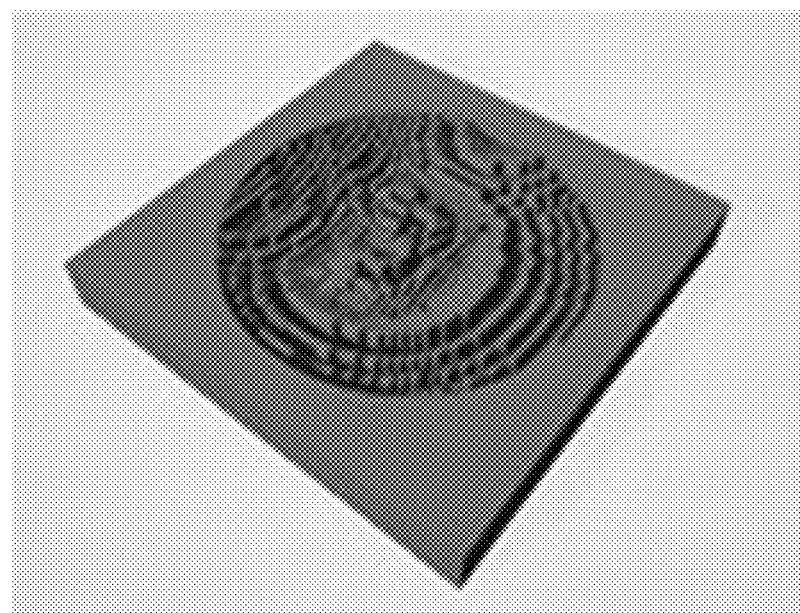

FIG. 4(c) is a view obtained by determining the thickness (height) for each unit area of the lens surface to be designed based on the phase value for each pixel in the phase distribution image derived in FIG. 4(b) described above, and three-dimensionally expressing the thickness. In this case, the lens material may also be considered. FIG. 4(d) illustrates the result of 3D modeling the lens based on FIG. 4(c). Such 3D modeling data may be derived as a 3D mesh model.

Such an ultrasonic hologram lens 150 may be manufactured by using the 3D printing method through the 3D mesh model generated based on the thickness of each unit area of the lens surface. That is, based on the determined thickness, the three-dimensional mesh model of the lens is generated, converted into a file capable of 3D printing, and input to the 3D printer to manufacture the lens.

Hereinafter, the principle of the deep learning algorithm according to the embodiment of the present disclosure used for lens design will be described in more detail.

Referring back to FIG. 2, the deep learning model used in the present disclosure performs the deep learning on the target image on which the set pattern shape is drawn, and outputs the phase value for each pixel as the two-dimensional phase distribution image.

Specifically, the U-Net deep learning model illustrated in FIG. 2 performs deep learning of the target image in which the amplitude value of the target acoustic field is individually assigned to each pixel corresponding to the set pattern shape (for example: ASK character), and outputs the phase distribution image in which the phase value for each pixel is expressed in color.

In the case of FIG. 2, a pixel portion in which the ASK character is drawn may have a higher amplitude value than a pixel portion in which the ASK character is not drawn.

Here, of course, pixel areas other than the ASK character may be allocated so that the amplitude value of the acoustic field becomes 0.

The amplitude value of the acoustic field for each pixel may be expressed as a matrix such as $A_{goal}(x,y)$. In this case, (x,y) corresponds to a coordinate point corresponding to each pixel. Also, the coordinate point of each pixel may have a meter unit to correspond to the actual coordinate system.

As described above, the input data of the U-Net is an image that draws a pattern to be formed at a desired distance (target surface) from the ultrasonic transducer, and each pixel value in the image means the amplitude in the acoustic field, so it may be expressed as $A_{goal}(x,y)$.

The learned U-Net-based model outputs the phase information as the result image (phase distribution image) so that this input image may be implemented in the two-dimensional plane. Each pixel value of the phase distribution image may be a negative number less than 0 as the phase value. In this case, the phase value of each pixel may be expressed as $\Phi_{TXDR}(x,y)$.

Thanks to the algorithm structure based on the U-Net, it is possible to predict the phase information quickly without iterative optimization. The calculation speed may vary depending on the size of the model and the size of the input image, such as the number of convolution layers, the number of kernels, and the size of the kernel, and it is constant other than that. For faster calculation speed, the size of the input image needs to be reduced, and for this purpose, interleave is used.

As illustrated in FIG. 3, the interleave layer reduces spatial resolution, that is, image size, and increases the number of channels while preserving the input image information. If the input image has H×W pixels and the image is interleaved into c×c blocks, the result is that the input image is rearranged by $$\frac{H}{c} \times \frac{W}{c} \times c^2.$$

The interleaved input image is output after being arranged in the original size of H×W through the opposite de-interleave layer at the end of the U-Net-based model. Through the interleave/de-interleave layer, the input image may be compressed and input to the U-Net, which may increase the calculation efficiency. In the embodiment of the present disclosure, the input image (192×192) is interleaved into 6×6 blocks, rearranged to 32×32×36, and input to the U-Net.

The U-Net-based model is learned to output the phase distribution image corresponding to the input of the input image, and is learned based on the loss function derived by using an Angular Spectrum Method (ASM) based on the output phase information rather than giving the correct answer.

Specifically, based on the phase value for each pixel in the phase distribution image output from the U-Net model of FIG. 2, an amplitude value $A_{ASM}(x,y)$ of the acoustic field for each pixel obtained when propagating the ultrasonic waves that are transmitted from the plane of the ultrasonic transducer to the target plane (target surface) through an angular spectrum method (ASM) is compared with the target amplitude value $A_{goal}(x,y)$ of the acoustic field for each pixel to learn in a direction to reduce the error. Here, any other ultrasonic waves simulation method may be used instead of the angular spectrum method.

A loss function corresponding to the error between the amplitude value $A_{goal}(x,y)$ of the acoustic field for each pixel of the original target input image and the amplitude value $A_{ASM}(x,y)$ of the acoustic field for each pixel obtained using the angle spectrum method may be expressed by Equation (1).

$$L(A_{goal}, A_{ASM}) = 1 - \left( \frac{\sum_{x,y} A_{goal} \circ A_{ASM}}{\sqrt{\left[\sum_{x,y} A_{goal}^2\right]\left[\sum_{x,y} A_{ASM}^2\right]}} \right) \quad \text{[Equation 1]}$$

Here, L is the loss function, and $\Sigma_{x,y}(\cdot)$ is a sum of values (·) obtained for each pixel. ∘ is a product between matrix elements, and since normalization is considered, even if the amplitude values are different, if the form of the $A_{goal}$ and the $A_{ASM}$ is the same, the error is 0. Learning may be proceeded by reducing this error to 0. For learning optimization, an adaptive moment estimation (ADAM) algorithm may be used.

The physical limitation block in FIG. 2 is a portion of adjusting the resolution of the phase distribution image, which illustrates the process of adjusting the resolution of the phase distribution image output from the U-Net to the processing resolution of the 3D printer. This will be described in more detail as follows.

Figure 5A:
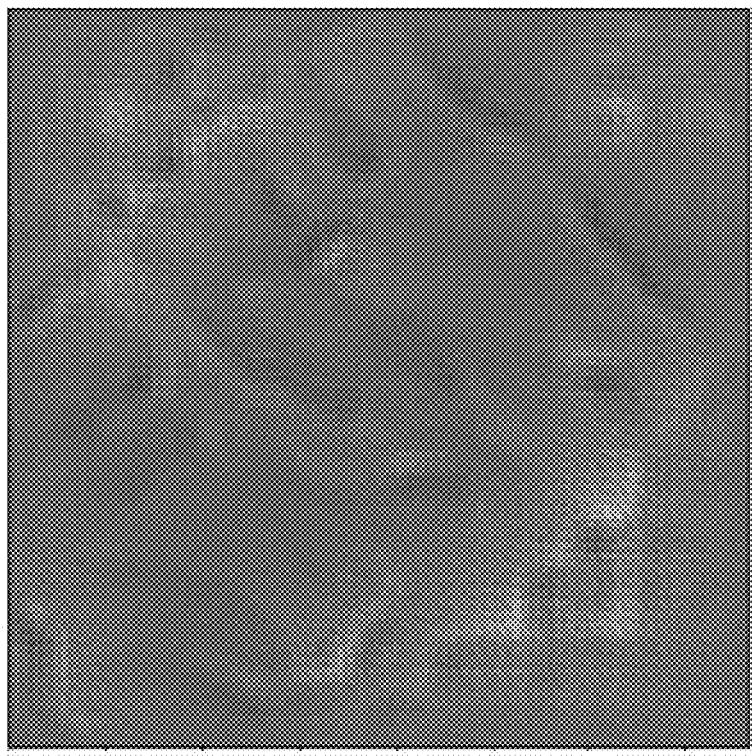
FIG. 5(a) and FIG. 5(b) are views illustrating a result of adjusting a resolution of a phase distribution image output from the U-Net model of FIG. 2 to a processing limit of a 3D printer through physical limitation.
Figure 5B:
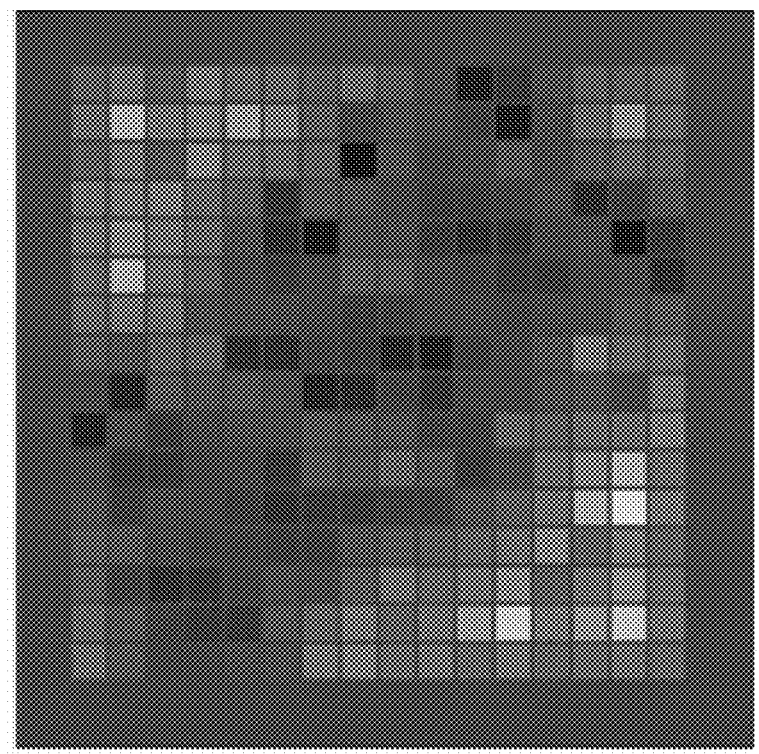

FIGS. 5(a) and 5(b) are views illustrating the result of adjusting the resolution of the phase distribution image output from the U-Net model of FIG. 2 to the processing limit of the 3D printer through physical limitations.

FIG. 5(a) illustrates the phase distribution image output from the U-Net-based model. If the resolution of the phase distribution image is 192×192 and the processing limit resolution is 16×16, the unit size of a sector (kernel) for smoothing processing is 12×12. There are 144 pixels per sector, and the individual phase values of 144 pixels in the same sector are all replaced with the average phase value thereof and may be smoothed.

As described above, the phase value of each pixel in the phase distribution image is smoothed for each sector, and the phase distribution for each pixel in the smoothed state, that is, the two-dimensional phase distribution image whose resolution is adjusted is used for deep learning.

The model construction through the learning of the deep learning algorithm illustrated in FIG. 2 may be performed by a controller in computer means including a processor, a memory, a user interface input/output device, and a storage device.

The deep learning model may be pre-learned through an input image of an arbitrary pattern shape. At this time, the shape of the pattern used for the input image is not particularly limited and may be various shapes such as circles, dots, characters, and geometric shapes, and may be simply learned as a circular pattern. If an input image of an arbitrary pattern is applied to the deep learning model that has been learned, a phase distribution image of the corresponding shape may be obtained.

Figure 6A:
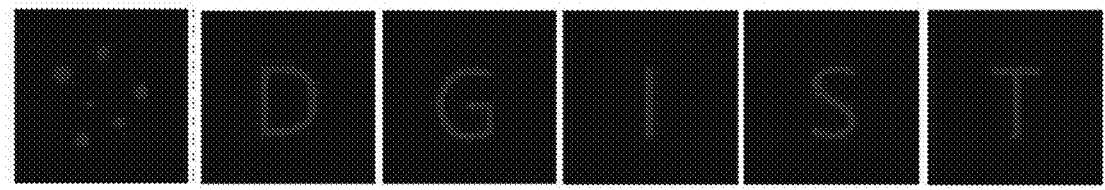
FIG. 6(a) and FIG. 6(b) are views illustrating simulation results predicted based on a phase distribution image derived when various patterns of target images are input to a learned deep learning model.
Figure 6B:

FIG. 6(a) and FIG. 6(b) are views illustrating simulation results predicted based on the phase distribution image derived when various patterns of target images are input to the learned deep learning model. From the results of FIG. 6(a) and FIG. 6(b), it may be confirmed that the phase is well determined for an image similar to the learning data.

In addition, it may be seen that even if learning is performed through the circular pattern, the phase is well determined to form the ultrasonic hologram even for a complex shape such as an English alphabet. This is a result illustrating that the deep learning-based ultrasonic hologram formation may not only form a hologram for a simply learned image, but may also be applied to other images, that is, it illustrates generalizability.

Figure 7A:
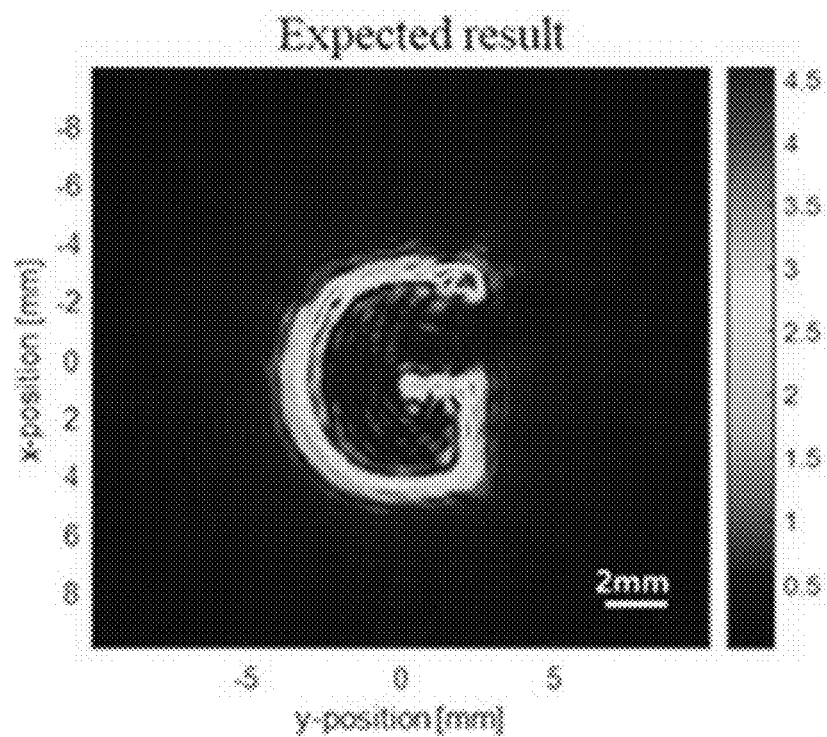
FIGS. 7(a) to 7(c) are views illustrating an ultrasonic hologram lens designed according to an embodiment of the present disclosure and performance thereof.
Figure 7B:
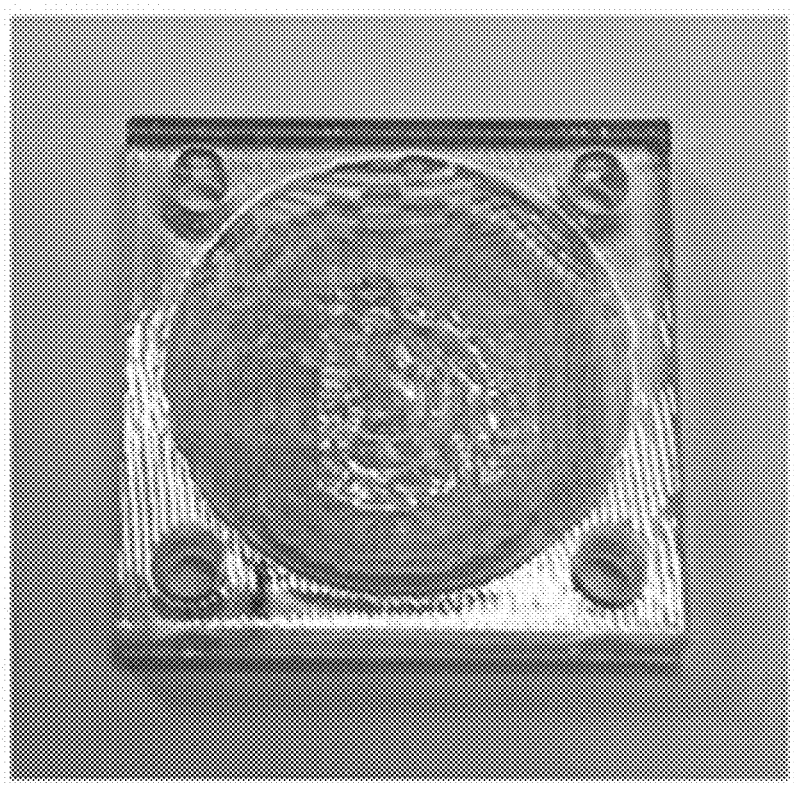
Figure 7C:
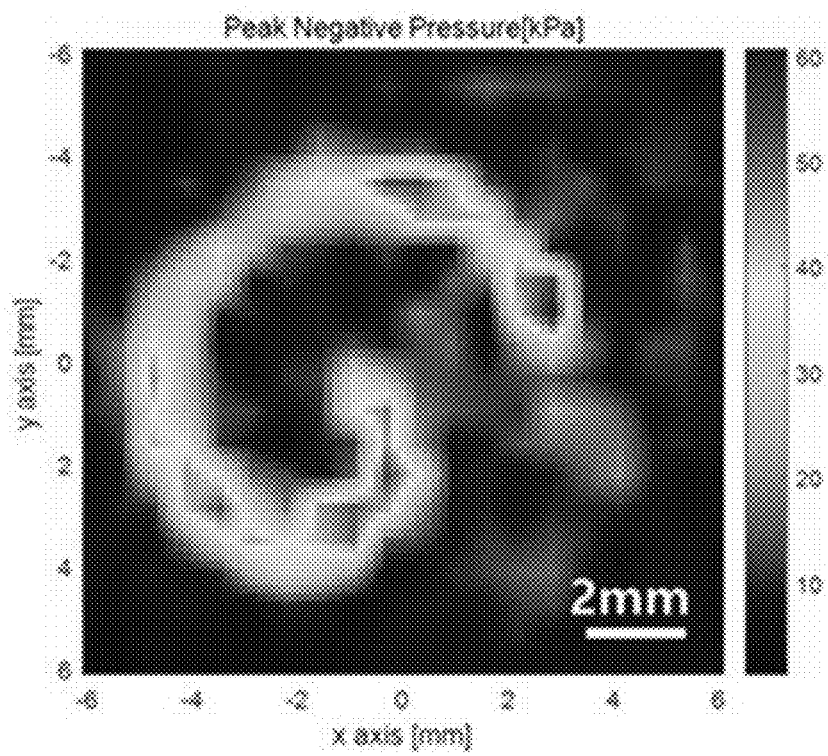

FIGS. 7(a) to 7(c) are views illustrating the ultrasonic hologram lens designed according to the embodiment of the present disclosure and its performance.

FIG. 7(a) is an ultrasonic hologram simulation result predicted through the phase distribution obtained through the deep learning algorithm, and illustrates a hologram result expected through the simulation. Based on the phase, it was simulated through a k-wave toolbox in MATLAB, and $P_{rms}$ was calculated from a time domain sound pressure that is the simulation result, and used for comparison. The plane generating the ultrasonic hologram was set to a plane 5 mm away from the transducer.

FIG. 7(b) illustrates the real ultrasonic hologram lens designed and manufactured based on the phase distribution obtained through the deep learning algorithm. It may be seen that the height is different for each unit area of the lens surface corresponding to the phase distribution determined by deep learning. FIG. 7(c) is an ultrasonic hologram result actually measured on the target surface by using an actually manufactured lens, and it may be seen that the predicted result and the actual measurement result illustrate a high degree of agreement with each other.

As described above, the present disclosure determines the thickness of each unit area of the lens surface according to the phase in consideration of the phase distribution result by the deep learning algorithm and the sound wave speed of the material to be used as the lens, and generates the three-dimensional mesh model of the lens based on the determined thickness, and may produce the lens by converting the 3D mesh model into a file that may be 3D printed. In addition, the simulation result through the phase distribution determined through the algorithm and the measurement result using the actually manufactured lens illustrate a high degree of agreement with each other.

Figure 8A:
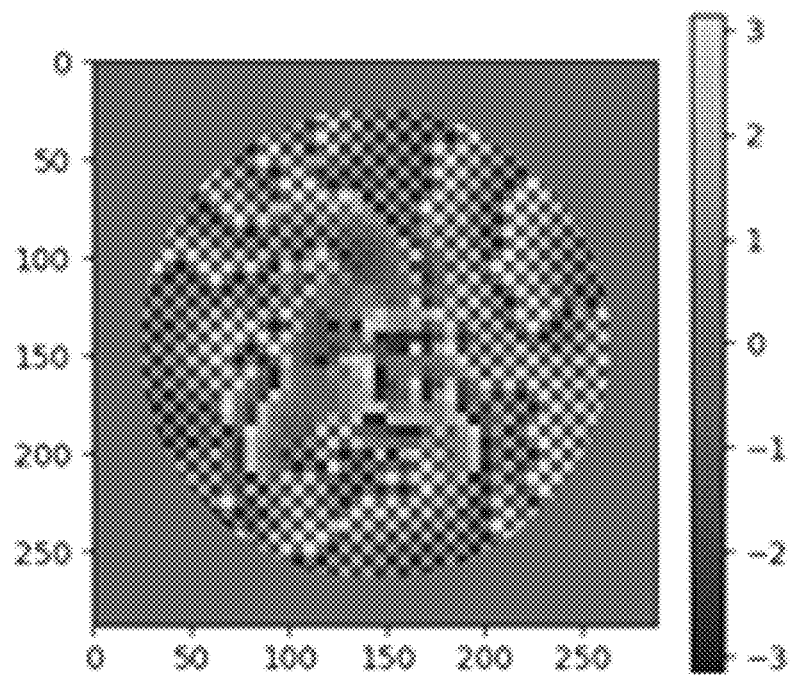
FIGS. 8(a) to 8(d) are views illustrating an ultrasonic hologram lens for multiple heights and simulation results according to an embodiment of the present disclosure.
Figure 8B:
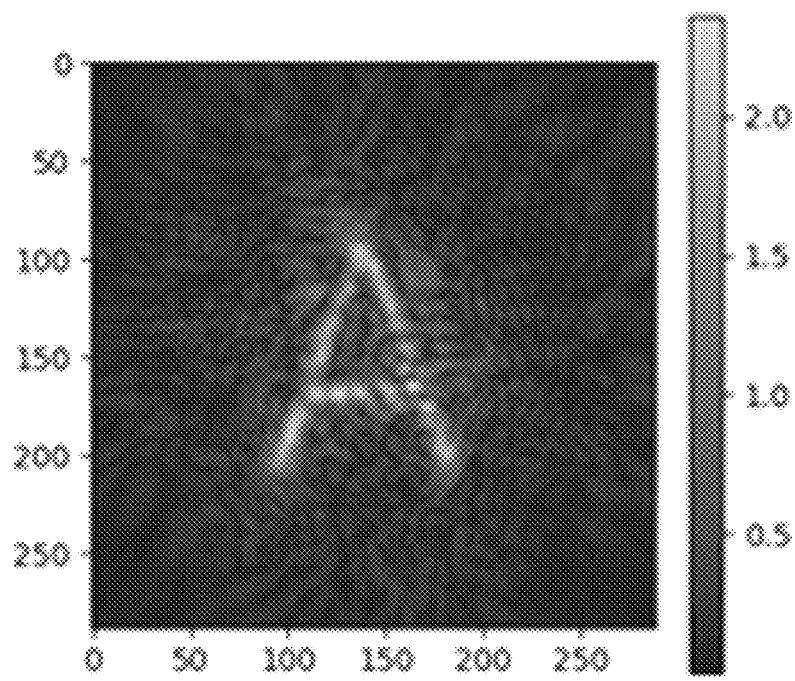
Figure 8C:
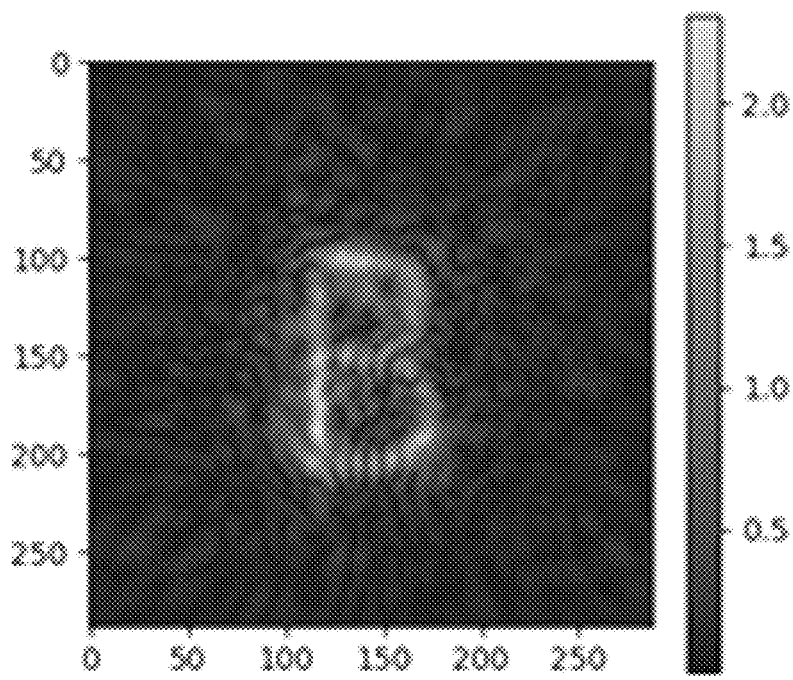
Figure 8D:
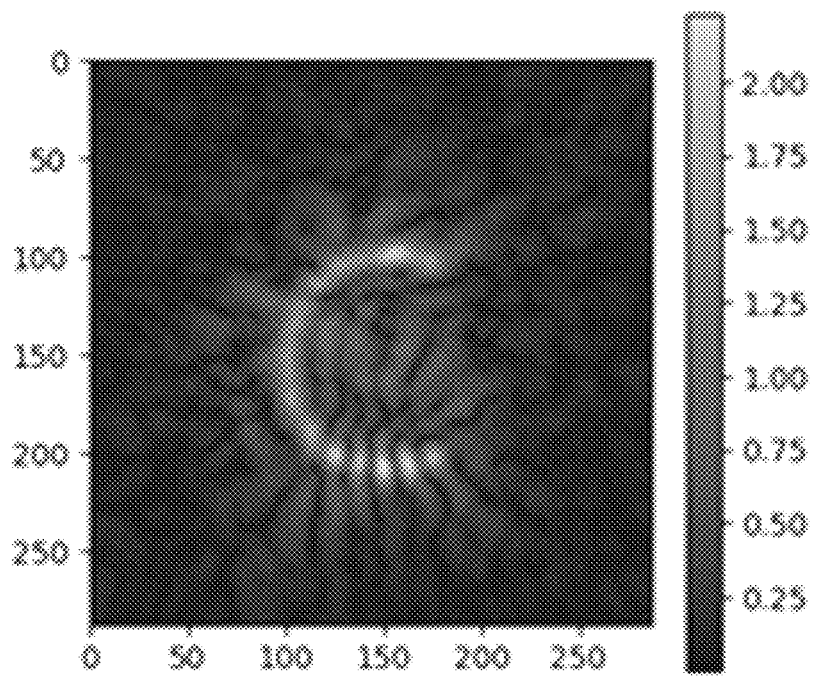

FIGS. 8(a) to 8(d) are views illustrating an ultrasonic hologram lens for multiple heights and simulation results according to an embodiment of the present disclosure. FIG. 8(a) is a result of optimizing the phase distribution by the algorithm, and FIGS. 8(b), (c), and (d) illustrate ultrasonic hologram results measured at a height of 2 mm, a height of 5 mm, and a height of 8 mm, respectively, based on the transducer plane. As described above, by using the present disclosure, holograms may be generated for multiple surfaces at multiple heights and may be applied to the three-dimensional cell culture and stimulation.

As described above, the present disclosure has an advantage of easy accessibility to be used for cell culture and stimulation because the ultrasonic hologram lens may be designed and manufactured by using the deep learning-based algorithm capable of quickly and easily deriving the phase distribution and being used for a desired purpose by changing the loss function, or the like. In addition, since it is possible to culture and stimulate the three-dimensional phase pattern, it may help in culturing or stimulating organoids.

Although the present disclosure has been described with reference to the embodiments illustrated in the drawings, which are only exemplary, those of ordinary skill in the art will understand that various modifications and equivalent other embodiments are possible therefrom. Accordingly, the true technical protection scope of the present disclosure should be defined by the technical spirit of the appended claims.

What is claimed is:

1. A cell stimulation and culture platform using an ultrasonic hologram, comprising:
    a culture vessel in which a culture well with an open lower portion is formed;
    a transmission sheet which is installed to cover a lower surface of the culture vessel and where a biological sample is seated on a surface portion corresponding to the culture well;
    a platform body of which an inner space is filled with a liquid ultrasonic medium and an open upper end is covered by the transmission sheet;
    an ultrasonic transducer that is installed at an inner lower end portion of the platform body in a state of being spaced apart from the biological sample by a set distance to generate ultrasonic waves upward; and
    an ultrasonic hologram lens that is installed on the ultrasonic transducer, transmits the incident ultrasonic waves to a target surface on which the biological sample is located through the ultrasonic medium, and spatially modulates the phase of the ultrasonic waves using a surface structure designed to have different height distributions to focus the ultrasonic waves in a set pattern shape on the target surface.

2. The cell stimulation and culture platform according to claim 1,
    wherein the biological sample is located on the target surface and cultured in the set pattern shape.

3. The cell stimulation and culture platform according to claim 1,
    wherein the transmission sheet is formed of a Mylar sheet or a PDMS sheet.

4. The cell stimulation and culture platform according to claim 1,
    wherein the ultrasonic medium is water or a material of which ultrasonic transmittance is greater than or equal to a threshold.

5. The cell stimulation and culture platform according to claim 1,
    wherein the ultrasonic hologram lens is designed based on a deep learning model that derives a phase distribution image to which a phase value for each pixel is assigned corresponding to an input of a target image in a form of the set pattern shape drawn, and
    a design thickness for each unit area of the lens surface varies according to a phase value for each pixel and a lens material.

6. The cell stimulation and culture platform according to claim 5,
    wherein the ultrasonic hologram lens is manufactured by a 3D printing method through a three-dimensional mesh model generated according to the thickness of each unit area of the lens surface.

7. The cell stimulation and culture platform according to claim 5,
    wherein the deep learning model performs deep learning of a target image where an amplitude value of a target acoustic field is individually assigned to each pixel corresponding to the set pattern shape, and outputs a phase value for each pixel as a two-dimensional phase distribution image.

8. The cell stimulation and culture platform according to claim 7, wherein the phase value for each pixel is determined in the −π to π ranges.

9. The cell stimulation and culture platform according to claim 7,
wherein the deep learning model is learned by using a loss between an amplitude value $A_{ASM}(x,y)$ of the acoustic field for each pixel derived on the target surface through an Angular Spectrum Method (ASM) or an arbitrary ultrasonic waves simulation based on the phase value for each pixel, and an amplitude value $A_{goal}(x,y)$ of the acoustic field for each pixel of the target image.

10. The cell stimulation and culture platform according to claim 9,
wherein a loss function corresponding to an error between the $A_{goal}(x,y)$ and the $A_{ASM}(x,y)$ is defined by the following equation:

$$L(A_{goal}, A_{ASM}) = 1 - \left( \frac{\sum_{x,y} A_{goal} \circ A_{ASM}}{\sqrt{\left[\sum_{x,y} A_{goal}^2\right]\left[\sum_{x,y} A_{ASM}^2\right]}} \right)$$

here, L is the loss function, is a product between matrix elements, and $\Sigma_{x,y}(\cdot)$ is a sum of values (·) obtained for each pixel.

11. The cell stimulation and culture platform according to claim 9,
wherein the phase value of each pixel in the phase distribution image is smoothed for each sector in accordance with a processing resolution of the 3D printer, and the phase value distribution for each pixel in the smoothed state is utilized for deep learning.

* * * * *